(12) United States Patent
McKinley et al.

(10) Patent No.: US 9,968,447 B2
(45) Date of Patent: May 15, 2018

(54) BIOPROSTHETIC TISSUE FOR USE AS A PROSTHETIC VALVE LEAFLET AND METHOD OF PREPARING

(71) Applicant: Medtronic Vascular, Inc., Santa Rosa, CA (US)

(72) Inventors: Laura McKinley, Santa Ana, CA (US); Benjamin Wong, Irvine, CA (US); Wei Wang, Garden Grove, CA (US); Elliot Howard, Aliso Viejo, CA (US); Tracey Tien, Reseda, CA (US); Karl Olney, Tustin, CA (US); Joshua Dudney, Mission Viejo, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 49 days.

(21) Appl. No.: 15/004,086

(22) Filed: Jan. 22, 2016

(65) Prior Publication Data
US 2017/0209262 A1 Jul. 27, 2017

(51) Int. Cl.
*A61F 2/24* (2006.01)

(52) U.S. Cl.
CPC .................................. *A61F 2/2415* (2013.01)

(58) Field of Classification Search
CPC ...... A61F 2250/0015; A61F 2250/0036; A61F 2250/0026; A61F 2/24; A61F 2/2415; A61F 2/2409; A61F 2/2418; A61F 2/2475; A61F 2249/00; A61F 2240/004; A61F 2240/005
USPC ....... 623/1.28, 1.32, 23.74, 1.24, 1.26, 2.14, 623/23.64, 23.68, 2.18
See application file for complete search history.

(56) References Cited

U.S. PATENT DOCUMENTS

| 6,174,331 B1* | 1/2001 | Moe ...................... A61F 2/2412 623/2.12 |
| 6,283,994 B1* | 9/2001 | Moe ...................... A61F 2/2412 623/2.12 |
| 6,475,239 B1* | 11/2002 | Campbell ............. A61F 2/2412 264/299 |
| 6,666,885 B2* | 12/2003 | Moe ...................... A61F 2/2412 623/2.12 |
| 7,141,064 B2* | 11/2006 | Scott ..................... A61F 2/2412 600/36 |
| 7,955,376 B2* | 6/2011 | Osborne ............... A61F 2/2418 623/1.24 |
| 8,597,687 B2* | 12/2013 | Daniel ................ A61L 27/3604 424/583 |
| 8,795,357 B2* | 8/2014 | Yohanan ............... A61F 2/2418 623/2.14 |

(Continued)

OTHER PUBLICATIONS

PCT/US2017/012883, The International Search Report and The Written Opinion of the International Searching Authority, dated Mar. 23, 2017, 11pags.

*Primary Examiner* — Alvin Stewart
(74) *Attorney, Agent, or Firm* — Dicke Billig & Czaja, PLLC

(57) ABSTRACT

Methods of preparing a sheet of bioprosthetic tissue for use as a prosthetic valve leaflet are disclosed. A method includes positioning a sheet of bioprosthetic tissue across an engagement face of a first patterned substrate. The engagement face defines a pattern having at least one raised region and areas of relief adjacent the at least one raised region. The tissue is compressed against the engagement face to deform the tissue to a deformed state corresponding with the pattern.

15 Claims, 4 Drawing Sheets

(56) References Cited

U.S. PATENT DOCUMENTS

| | | | |
|---|---|---|---|
| 8,846,390 B2 | 9/2014 | Dove et al. | |
| 8,945,212 B2* | 2/2015 | Bruchman | A61F 2/2415 623/2.42 |
| 9,615,922 B2* | 4/2017 | Munnelly | A61F 2/2415 |
| 9,795,475 B2* | 10/2017 | Bruchman | A61F 2/24 |
| 2002/0045936 A1* | 4/2002 | Moe | A61F 2/2412 623/2.17 |
| 2003/0212454 A1* | 11/2003 | Scott | A61F 2/2412 623/2.14 |
| 2004/0056479 A1* | 3/2004 | Fox | B42C 1/10 283/101 |
| 2005/0187614 A1* | 8/2005 | Agnew | A61F 2/2418 623/1.24 |
| 2005/0211680 A1* | 9/2005 | Li | A61F 2/0077 219/121.68 |
| 2006/0276888 A1 | 12/2006 | Lee et al. | |
| 2008/0131473 A1* | 6/2008 | Brown | A61L 27/24 424/423 |
| 2010/0023119 A1* | 1/2010 | Yeo | A61F 2/2415 623/2.14 |
| 2011/0000073 A1* | 1/2011 | O'Fallon | A61F 2/2415 29/464 |
| 2012/0323315 A1* | 12/2012 | Bruchman | A61F 2/2415 623/2.17 |
| 2013/0110097 A1 | 5/2013 | Schneider et al. | |
| 2013/0116676 A1 | 5/2013 | Tian et al. | |
| 2013/0197631 A1* | 8/2013 | Bruchman | A61L 27/34 623/2.17 |
| 2013/0310929 A1 | 11/2013 | Dove et al. | |
| 2013/0325117 A1* | 12/2013 | Bruchman | A61L 27/48 623/2.17 |
| 2014/0257472 A1* | 9/2014 | Kutty | A61F 2/2415 623/2.13 |
| 2015/0091219 A1* | 4/2015 | Munnelly | A61F 2/2415 264/479 |
| 2015/0209128 A1* | 7/2015 | Markman | A61F 2/0077 623/23.72 |
| 2016/0067038 A1* | 3/2016 | Park | A61F 2/2406 623/2.18 |
| 2016/0235527 A1* | 8/2016 | Sanders | A61F 2/2415 |
| 2016/0317295 A1* | 11/2016 | Jana | A61F 2/2415 |
| 2017/0231758 A1* | 8/2017 | Bruchman | A61F 2/2415 156/331.7 |
| 2017/0340439 A1* | 11/2017 | Tsubouchi | A61F 2/2496 |

* cited by examiner

BIOPROSTHETIC TISSUE FOR USE AS A PROSTHETIC VALVE LEAFLET AND METHOD OF PREPARING

BACKGROUND

Various types and configurations of prosthetic heart valves are used to replace diseased natural human heart valves. The actual shape and configuration of any particularly prosthetic heart valve is dependent to some extent upon the valve being replaced (i.e., mitral valve, tricuspid valve, aortic valve, or pulmonary valve). In general, the prosthetic heart valve designs attempt to replicate the function of the valve being replaced and thus will include valve leaflet-like structures used with either bioprosthesis or mechanical heart valves prosthesis.

A prosthetic heart valve encompasses bioprosthetic valves having leaflets made of a biological material, for example, harvested porcine valve leaflets, or bovine or equine or porcine pericardial leaflets. Bioprosthetic valves may be formed by shaping a plurality of individual flexible leaflets out of bovine or porcine tissue or other materials, and combining the leaflets to form the valve. One advantage of bioprosthetic valves, unlike mechanical valves, is that the patient receiving the valve typically does not require long term treatment with anticoagulants.

Valves using flexible leaflets, such as those made of bovine pericardial tissue, for example, can be composed of radially expandable stents with flexible leaflets attached. Implant methods include compressing the valve radially by a significant amount to reduce its diameter or delivery profile, inserting the valve into a delivery tool, such as a catheter or cannula, and advancing the delivery tool to the correct anatomical position in the heart. Once properly positioned, the valve is deployed by radial expansion within the native valve annulus, either through self-expanding stent structure or with an expansion balloon. The collapsed valve in the catheter may be introduced through the vasculature, such as through the femoral artery, or more directly through an intercostal incision in the chest.

When a valve is loaded into a delivery device, the valve has to be crimped down to a reduced or compressed size. When the valve is crimped down, the leaflets have to compact and fold in a manner such that the leaflets collapse within the space available within the crimped stent formation. As a transcatheter device is crimped the tissue typically folds in an uncontrolled manner causing the tissue to be pinched by the frame diamonds. This pinching could cause damage to the tissue and increases the packing density of the device. Controlling the manner of the tissue folds and reducing the tissue thickness would reduce the crimp profile for transcatheter valve designs.

SUMMARY

One aspect of the present disclosure includes a method of preparing a sheet of bioprosthetic tissue for use as a prosthetic valve leaflet. The method includes positioning a sheet of bioprosthetic tissue across an engagement face of a first patterned substrate, the engagement face defining a pattern having at least one raised region and areas of relief adjacent at least one raised region and compressing the tissue against the engagement face to deform the tissue to a deformed state corresponding with the pattern.

Another aspect of the present disclosure includes a method of preparing a sheet of bioprosthetic tissue. The method includes extending a sheet of tissue across a patterned surface of a first substrate and removably securing the sheet of tissue to the patterned surface. The method also includes applying a force to press the tissue against the patterned surface to compress the tissue and reduce tissue thickness in select areas corresponding to the patterned surface and treating the tissue with a fixative.

Another aspect of the present disclosure includes conditioned bioprosthetic tissue. The conditioned bioprosthetic tissue includes a sheet of bioprosthetic tissue having a first major surface and a second major surface. The first major surface has a pattern including at least one depressed region and areas of relief adjacent to the at least one depressed region. The at least one depressed region has a first tissue density that is greater than a second tissue density of the areas of relief.

DETAILED DESCRIPTION

The present disclosure is directed to the preparation of bioprosthetic material for cardio implantation, such as implantation as a prosthetic heart valve. Any tissue that has a suitable durability and elasticity is a candidate, though those of skill in the art will appreciate that certain materials may be better suited for any one specific application. In general, tissues that contain fibrous collagen and elastic fibers or elastin may be suitable for use in fabricating heart valve leaflets. Bioprosthetic tissue such as bovine, porcine, equine, and other mammalian pericardium, including human, may be used. Furthermore, tissue from other anatomical sources may be used, such as dura mater, peritoneum, diaphragm, small intestine submucosa or others. Other potential types of collagen that can be used are hybrid natural collagen solution or electrospun collagen elastic fabric. Additionally, certain engineered tissue may be used, such as those synthesized by growing collagenous tissue over a mesh frame or scaffold.

Figure 1:
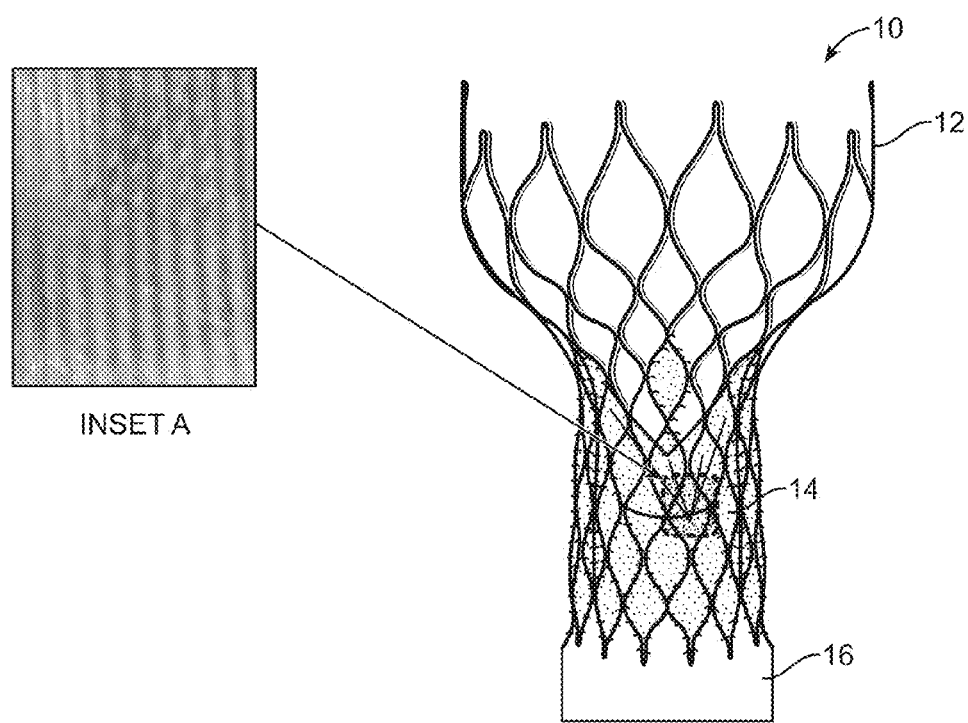
FIG. 1 is a side view of a prosthetic heart valve in accordance with aspects of the present disclosure.

FIG. 1 illustrates a side view of a prosthetic heart valve 10 in accordance with aspects of the present disclosure. The prosthetic heart valve 10, in particular an expandable heart valve, generally includes a structural frame, or stent 12, a flexible leaflet structure 14 supported by the stent 12. In some embodiments, a flexible skirt 16 can be included and secured to an outer surface of the leaflet structure 14. Various tissues can be used for the valve leaflets 14 or valve skirts 16. The prosthetic heart valve 10 and stent 12 are configured to be radially collapsible to a collapsed or crimped state for introduction into the body on a delivery catheter and radially expandable to an expanded state for implanting the valve 10 at a desired location in the body (e.g., the native aortic valve). Various materials are suitable for the stent 12, such as nickel-titanium alloys (i.e., Nitinol), for example. Notably, various stent body 12 configurations and constructions are suitable in accordance with aspects of the present disclosure. The leaflets 14 incorporated in expandable prosthetic heart valves 10 are initially crimped into a small delivery profile or diameter to be passed through a catheter or other delivery systems and then expanded at the implantation site, typically a valve annulus.

A number of steps are involved in the commercial process of preparing bioprosthetic tissue for use in cardio implantation, in particular, use in prosthetic heart valves as leaflets or skirts. An initial step, occurring as soon as possible after harvesting the tissue from a biological source, includes receiving and initial cleaning the tissue of muscle tissue. After the initial cleaning of the tissue, the tissue is dissected and further cleaned of adherent fat or loose connective tissue.

Inset A illustrates an example of a patterned leaflet used in a prosthetic heart valve 10 in accordance with aspects of the present disclosure. Patterning the leaflets 14 is included within the central region of the valve frame 12, making collapsing of the valve 10 easier with minimal force. The patterns in the leaflet 14 form creases, as described in greater detail below, that enable the tissue to fold in a desired manner by increasing the likelihood that the tissue will bend at particular crease locations providing a patterned valve leaflet 14 that will fold down in a desired manner.

An external skirt 16 may be included on the valve 10. Similar to the leaflets 14, the tissue included in the skirt 16 can be patterned. The external skirt 16 can be included in order to address issue of a para valvular leak (PVL). The patterning of the tissue included in the valve skirt 16 increases surface area of tissue exposed. With the additional tissue surface area formed by the pattern a sealing blood response may be started. The additional surface area can increase the seal and the likelihood of reducing the PVL. In one embodiment, the skirt 16 includes a deformed first surface that is exposed to the blood flow and a smooth, or substantially planar, second surface that is attached against the stent frame. The deformed tissue surface(s) are discussed in greater detail below.

Figure 2A:
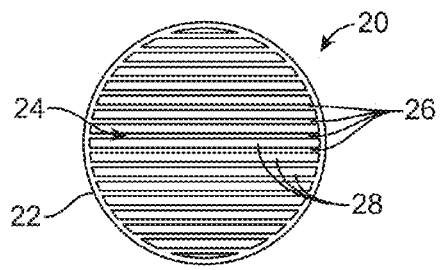
FIG. 2A is a top view of a patterned substrate used to form patterned tissue in accordance with aspects of the present disclosure.

FIG. 2A is a top view of a patterned substrate 20 used to form patterned tissue in accordance with aspects of the present disclosure. The patterned substrate 20 includes a perimeter 22 and an engagement face 24 extending within the perimeter 22. With additional reference to FIG. 2B, the engagement face 24 is suitable for positioning a sheet of bioprosthetic tissue across. The engagement face 24 defines a pattern having at least one raised region 26 and areas of relief 28 adjacent the at least one raised region 26. The patterned substrate 20 includes areas of relief 28, such as openings extending through the substrate 20, from the engagement face 24 to an opposing second face (not shown). The patterned substrate 20 can include bars as the raised regions 26 extending across the substrate 20 in a variety of patterns. The raised regions 26 (e.g., bars) can be parallel, for example, or any other suitable configuration. The raised regions 26 can extend various depths from the engagement face 24 of the patterned substrate 20 imparting compression to the tissue 30 of corresponding depths. The engagement face 24 of the substrate 20, and thus also the resultant deformed tissue, includes contours in specific localized areas.

Figure 2B:
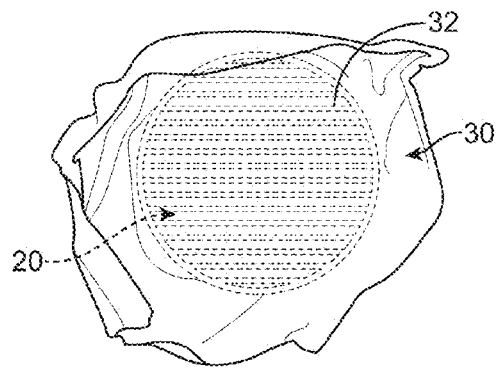
FIG. 2B is a top view of a sheet of bioprosthetic tissue positioned on the patterned substrate in accordance with aspects of the present disclosure.

FIG. 2B is a top view of a sheet of bioprosthetic tissue 30 positioned on the patterned substrate 20 in accordance with aspects of the present disclosure. The sheet of bioprosthetic tissue 30 is positioned across with a first major surface 34 positioned in contact against the engagement face 24 of the patterned substrate 20 and a second major surface 32 opposite the first major surface 34 (see, e.g., FIG. 2C). The tissue 30 is pressed, or compressed, against the engagement face 24 to deform, or create imprints in, the tissue to a desired pattern corresponding with the pattern formed at the engagement face 24. As discussed above, the resultant sheet of tissue in the deformed state is more readily foldable along the regions of reduced thickness as compared to other regions of the sheet of tissue.

Figure 2C:
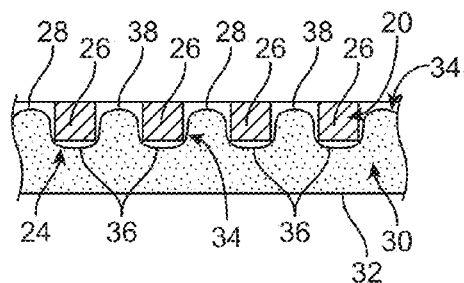
FIGS. 2C-2D are cross-sectional illustrations of a sheet of bioprosthetic tissue prepared using a patterned substrate.
Figure 2D:
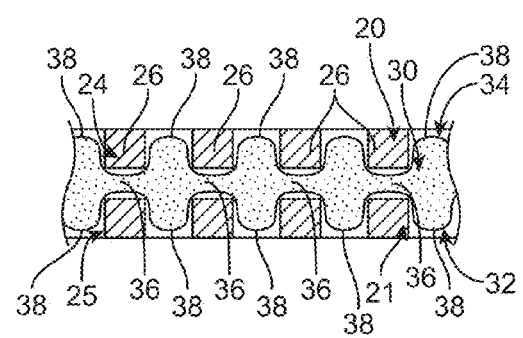

FIGS. 2C and 2D illustrate partial cross-sections of the bioprosthetic tissue 30 prepared in accordance to aspects of the present disclosure. FIG. 2C illustrates a partial cross-section of FIG. 2B with the first major surface 34 of the bioprosthetic tissue 30 compressed against the first patterned substrate 20. Compressing the tissue against the engagement face 24 imparts a pattern into the first major surface 34 corresponding with the pattern of the engagement face 24 and increases tissue density in the selectively compressed pattern areas. The deformed state of the tissue includes regions of reduced tissue thickness and increased tissue density corresponding to the at least one raised region 26. FIG. 2D illustrates a second patterned substrate 21 similar to the first patterned substrate 20 positioned against the tissue 30 opposite the first patterned substrate 20. In one embodiment, the first and second patterned substrates 20, 21 can have matching patterns, with the engagement surfaces 24, 25 aligned on opposite surfaces 32, 34 of the tissue 30 to compress the tissue 30 at aligned selected regions. Alternatively, the first patterned substrate 20 is a positive pattern and the second patterned substrate 21 is a negative pattern having relief areas opposite to those of the first patterned substrate 20. The tissue can be compressed between the first and second patterned substrates 20, 21 to deform opposing surfaces 32, 34 of the tissue 30. The deformed tissue includes varying tissue thickness corresponding, or complimentary to, the patterned substrates 20, 21. The deformed tissue includes projections and recesses, or deviations, from a planar surface. The first major surface 34 of the tissue 30 has a pattern including at least one depressed region 36 and areas of relief 38 adjacent to the at least one depressed region 36. A density of the tissue at the at least one depressed region 36 has a first tissue density that is greater than a second tissue density of the areas of relief 38. The deformed tissue can include planar deviations on one or both major surfaces 32, 34. For instance, the tissue surface can include a wave or waves of grooved, compressed deviations. In other words, either one or both of the opposing major tissue surfaces 32, 34 are non-planar.

Figure 3A:
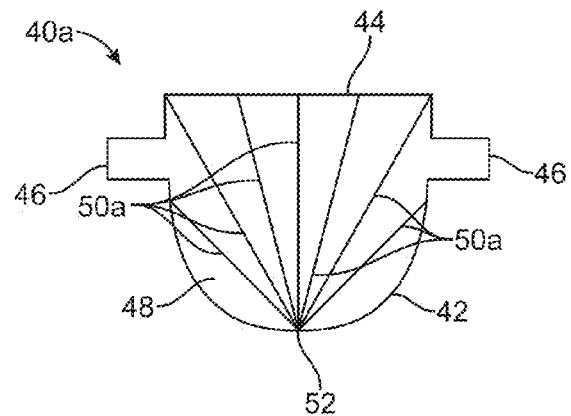
FIGS. 3A-3C are exemplary bioprosthetic tissue patterns in accordance with aspects of the present disclosure.
Figure 3B:
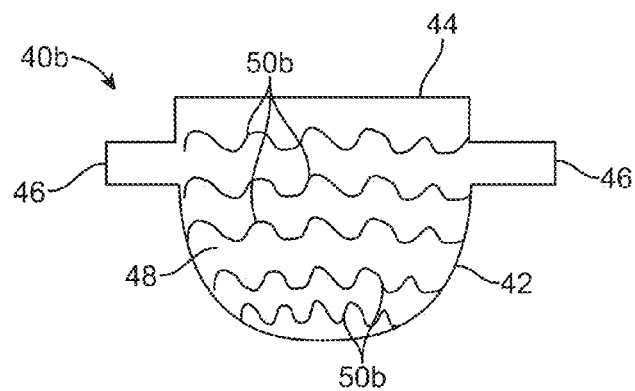
Figure 3C:
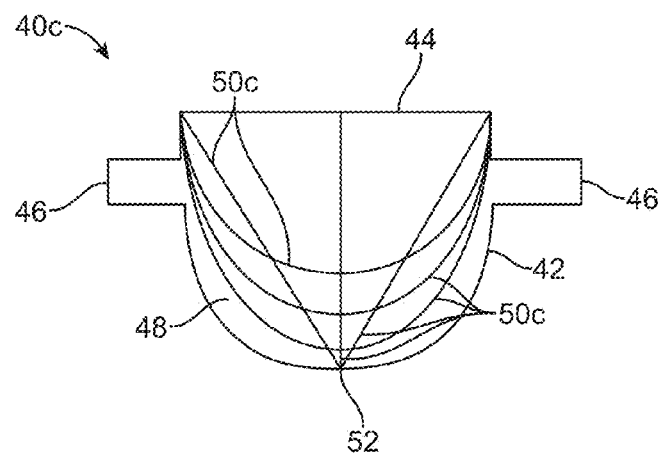

FIGS. 3A-3C illustrate a few exemplary patterned leaflets. The patterned, or deformed, tissue can be cut to form a leaflet of a prosthetic valve after the tissue is fixated. Each of the leaflets 40a, 40b, 40c are illustrated in top view and has an arcuate cusp edge 42, a generally straight free edge 44 opposite the cusp edge 42, and a pair of oppositely-directed tabs 46 at either end of the free edge 44. A central portion 48 in each of the leaflets 40 forms the fluid occluding surface that oscillates in and out of the flow stream to alternately open and close the valve. The shapes illustrated are exemplary only, and other leaflet shapes can be used. The patterns illustrated in the central portions 48 of the leaflets are in no way meant to be limiting, as various additional pattern formations are contemplated with this disclosure.

Lines indicate locally thinned areas of the tissue formed by applying compression at selected regions as discussed above and below. The geometry of a tissue pattern can be configured to optimize the crease line configuration to complement a particular stent frame. For example, FIG. 3A illustrates a leaflet pattern including compressed lines 50*a* of tissue in a radial pattern projecting from a central point 52 of the cusp edge 42. In another embodiment illustrated in FIG. 3B, compressed lines 50*b* of tissue are in wavelike form, extending generally from tab 46 to tab 46 across the central portion 48. In another embodiment, as illustrated in FIG. 3C, the compressed lines 50*c* of tissue are overlapping semicircular and radial.

Figure 4A:
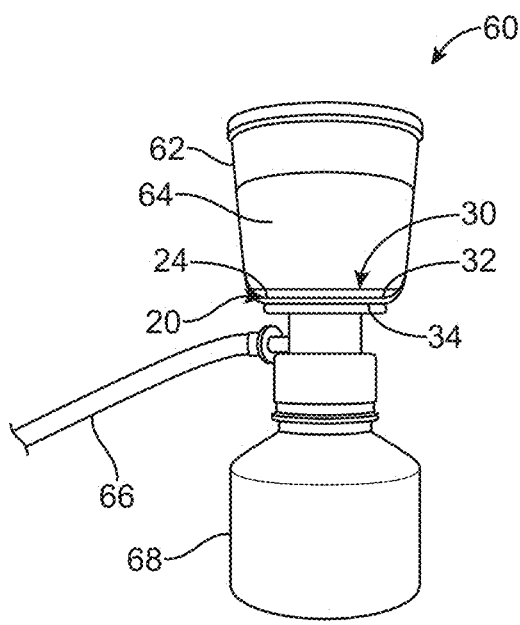
FIG. 4A is a side view of a system useful in patterning bioprosthetic tissue in accordance with aspects of the present disclosure.
Figure 4B:
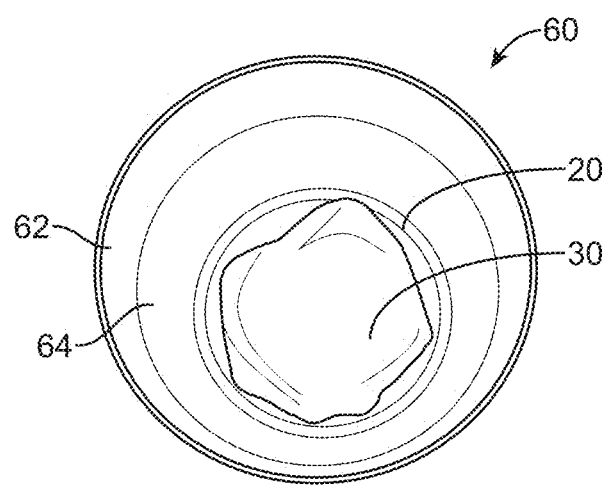
FIG. 4B is a top view of the system useful in patterning bioprosthetic tissue of FIG. 4A in accordance with aspects of the present disclosure.

FIG. 4A is a side view of a system 60 useful in patterning the bioprosthetic tissue in accordance with aspects of the present disclosure. FIG. 4B is a top view of the system 60 useful in patterning bioprosthetic tissue 30 of FIG. 2B. A sheet of tissue 30 is extended cross and removably secured to the patterned engagement face 24 of the patterned substrate 20 of FIG. 2A and positioned in a first vessel 62. A second vessel 68 is fluidly connected to the first vessel 62 opposite the patterned substrate 20. The tissue 30 can be placed in a fixative solution 64 for fixation of the tissue. Fixation of the tissue causes cross-linking of the collagen and the protein-like compounds associated with the collagen and is performed to preserve the ultra-structure of the connective tissue. The fixative solution 64, such as glutaraldehyde, can be poured onto a surface 32 of the tissue 30 opposite the first patterned substrate 20. Fixation can be accomplished using a glutaraldehyde or other suitable fixative. The tissue 30 is treated with the fixative 64 during and/or after the force is applied to fixate, or lock the deformed surface pattern in the tissue. A force is applied to press the tissue 30 against the engagement face 24 to compress the tissue 30 and reduce tissue thickness in select areas corresponding to the patterned engagement face 24. A vacuum 66 can be used to create suction along a second surface 34 of the sheet of tissue 30. The suction force can be applied to in order to compress the tissue 30 against the engagement face 24 of the first patterned substrate 24. The vacuum 66 can pull the fixative 64 through the tissue 30 and the patterned substrates 20 into the second, or lower, vessel 68. The fixative 64 can be pulled through the tissue 30 to fixate the patterned, or deformed, surface of the tissue 30 by the suction force. The fixative 64 can fixate the deformed contours along the surface 34 if a first substrate 20 is positioned along the second surface 34, or both the surfaces 32, 34 if both the first and second substrates 20, 21 are used, as the fixative 64 passes through the tissue 30. The second surface 34 of the tissue is deformed via selectively compressed focused regions in a pattern corresponding to the patterned surface of the first patterned substrate as illustrated in FIGS. 3A-3C. In one embodiment, a heating element is applied to the tissue along with pressure to locally thin the tissue at select regions. The tissue can be locally thinned by compression of the heating element to select areas to create patterns in the tissue.

Although the present disclosure has been described with reference to preferred embodiments, workers skilled in the art will recognize that changes can be made in form and detail without departing from the spirit and scope of the present disclosure.

What is claimed is:

1. A method of preparing a sheet of bioprosthetic tissue for use as a prosthetic valve leaflet, comprising:
    positioning a sheet of bioprosthetic tissue across an engagement face of a first patterned substrate, the engagement face defining a pattern having at least one raised region and areas of relief adjacent the at least one raised region, wherein the areas of relief define openings extending from the engagement face to a face opposite the engagement face; and
    compressing the tissue against the engagement face to deform the tissue to a deformed state corresponding with the pattern.

2. The method of claim 1, wherein the step of positioning includes bringing a first major surface of the sheet of bioprosthetic tissue into contact with the engagement face, and further wherein the step of compressing the tissue includes imparting a pattern into the first major surface corresponding with the pattern of the engagement face.

3. The method of claim 1, wherein the deformed state of the tissue includes regions of reduced thickness corresponding to the at least one raised region.

4. The method of claim 3, wherein the deformed state includes the sheet of tissue being more readily folded along the regions of reduced thickness as compared to other regions of the sheet of tissue.

5. The method of claim 1, further comprising:
    positioning a second patterned substrate against the tissue opposite the first patterned substrate.

6. The method of claim 5, wherein the step of compressing further includes:
    compressing the tissue between the first and second patterned substrates to deform opposing surfaces of the tissue.

7. The method of claim 1, wherein the step of compressing the tissue against the first patterned substrate includes applying a suction force to the tissue to pull the tissue toward the first patterned substrate.

8. The method of claim 1, wherein after the step of compressing, the method further comprising:
    pulling a fixative fluid through the tissue to fixate the deformed surface of the tissue.

9. The method of claim 1, wherein after the step of compressing, the method further comprising:
    treating the tissue with a fixative to fixate the tissue in the deformed state.

10. The method of claim 1, further comprising: heating the tissue to locally thin the tissue at select regions.

11. A method of preparing a sheet of bioprosthetic tissue, comprising:
    extending a sheet of tissue across a patterned surface of a first substrate;
    removably securing the sheet of tissue to the patterned surface;
    applying a force to press the tissue against the patterned surface to compress the tissue and reduce tissue thickness in select areas corresponding to the patterned surface; and
    treating the tissue with a fixative,
    wherein the application of force is facilitated by a vacuum source.

12. The method of claim 11, further comprising:
    positioning a second substrate against the sheet of tissue opposite the first substrate;
    compressing the tissue between the first and second substrates to deform opposing surfaces of the tissue.

13. The method of claim 11, further comprising:
    cutting the tissue to form a leaflet of a prosthetic valve after treating the tissue.

14. The method of claim 11, wherein treating the tissue with the fixative includes passing the fixative through the tissue.

15. The method of claim 11, further comprising: applying a heating element to the tissue to locally thin the tissue at select regions.

* * * * *